US00PP16532P2

(12) United States Plant Patent
Spanton

(10) Patent No.: US PP16,532 P2
(45) Date of Patent: May 9, 2006

(54) ***FUCHSIA* PLANT NAMED 'ROSE QUARTET'**

(50) Latin Name: *Fuchsia×hybrida*
Varietal Denomination: Rose Quartet

(76) Inventor: Christopher John Spanton, Four Oaks, Farm Lane Lower Withington, MacClesfield, Cheshire (GB), SK11 9DU ( * ) Notice: Subject to any disclaimer, the term of this patent is extended or adjusted under 35 U.S.C. 154(b) by 61 days.

(21) Appl. No.: 11/056,986

(22) Filed: Feb. 14, 2005

(51) Int. Cl.
*A01H 5/00* (2006.01)

(52) U.S. Cl. ..... Plt./300

(58) Field of Classification Search ..... Plt./300
See application file for complete search history.

*Primary Examiner*—Anne Marie Grunberg
*Assistant Examiner*—June Hwu

(57) ABSTRACT

A new cultivar of *Fuchsia* plant named 'Rose Quartet', characterized by compact mounding habit, yellow-grown leaves, gray-red stems, and pink flowers with a quartered corolla and reflexed sepals. In combination these traits set 'Rose Quartet' apart from all other existing varieties of *Fuchsia* known to the inventor.

2 Drawing Sheets

Genus: *Fuchsia*.
Species: ×*hybrida*.
Denomination: Rose Quartet.

BACKGROUND OF THE INVENTION

The present invention relates to a new and distinct variety of *Fuchsia* grown for use as an ornamental for container, hanging basket and the landscape. The new cultivar is known botanically as *Fuchsia×hybrida* and will be referred to hereinafter by the cultivar name 'Rose Quartet'.

The new cultivar 'Rose Quartet' is a chance hybrid which was discovered by the inventor as individual whole plant within a population of unnamed and unreleased hybrid plants which resulted from a formal breeding program conducted by the inventor in a cultivated area of Cheshire, England. The purpose of the breeding program was to create new showy *Fuchsia* that exhibit reliable commercial performance, compact bushy growth habit, as well as new and unique flowers. The program was established in 1997. Induced multiple open cross-pollinations of up to 200 per year have occurred since that time, between individual plant crops of up to forty individual commercial hybrids of *Fuchsia*, and involving 2–3 million individual plants.

Seed was collected from numerous crosses, and sown, in order to observe the resulting seedlings. In 2000 the inventor selected 'Rose Quartet', from the seedlings, based on its unique flower traits. The exact parents are unknown. The female parent plant is an individual unnamed *Fuchsia* in an individual crop of *Fuchsia×hybrida*. The male parent plant is an individual unnamed *Fuchsia* in an individual crop of *Fuchsia×hybrida*. There are no close comparison plants known to the inventor. The new variety 'Rose Quartet' is an ornamental plant characterized by compact mounding habit, yellow-green leaves, gray-red stems, and pink flowers with a quartered corolla and re-flexed sepals.

'Rose Quartet' was first asexually propagated, in June 2000, by the inventor in a cultivated area of Cheshire, England. The method of propagation used was softwood cuttings. The characteristics of the new *Fuchsia* cultivar named 'Rose Quartet' have been determined stable and are reproduced true to type in successive generations.

SUMMARY OF THE INVENTION

The following traits have been repeatedly observed and represent the distinguishing characteristics of the new variety 'Rose Quartet'. In combination these traits set 'Rose Quartet' apart from all other *Fuchsia* known to the inventor. 'ROSE QUARTET' has not been tested under all possible conditions and phenotypic differences may be observed with variations in environmental, climatic and cultural conditions, however, without any variance in genotype.

1. *Fuchsia* 'Rose Quartet' exhibits compact mounding habit.
2. *Fuchsia* 'ROSE QUARTET' exhibits pink flowers.
3. *Fuchsia* 'ROSE QUARTET' exhibits pale green and white re-flexed sepals.
4. The flower of *Fuchsia* 'ROSE QUARTET' exhibits a quartered corolla.
5. *Fuchsia* 'ROSE QUARTET' exhibits yellow green leaves.
6. *Fuchsia* 'ROSE QUARTET' exhibits gray-red stems.
7. *Fuchsia* 'ROSE QUARTET' is propagated using softwood cuttings.
8. *Fuchsia* 'ROSE QUARTET' is hardy in USDA Zone 8b.
9. *Fuchsia* 'ROSE QUARTET' is 30–45 cm. in height and 25–35 cm. in width at maturity.

BRIEF DESCRIPTION OF THE DRAWINGS

The accompanying color drawings illustrate the overall appearance of the new cultivar 'Rose Quartet' showing the colors as true as it is reasonably possible to obtain in colored reproductions of this type. Colors in the drawings may differ from the color values cited in the detailed botanical description, which accurately describe the actual colors of the new variety 'Rose Quartet'. Plants in the drawings are 5-months-old and were greenhouse grown in Arroyo Grande, Calif. in one-liter containers.

The drawing labeled

The drawing labeled

Figure 1:
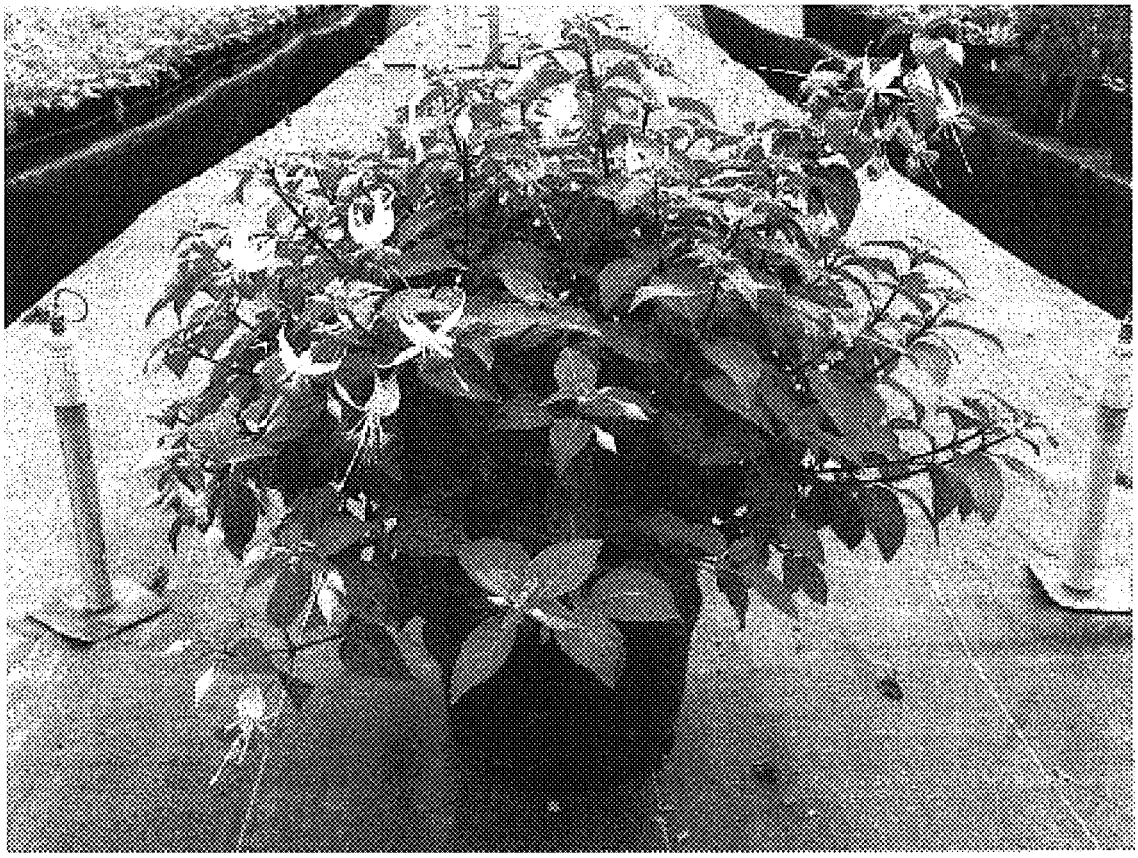
FIG. 1 illustrates the entire plant from a side perspective.
Figure 2:
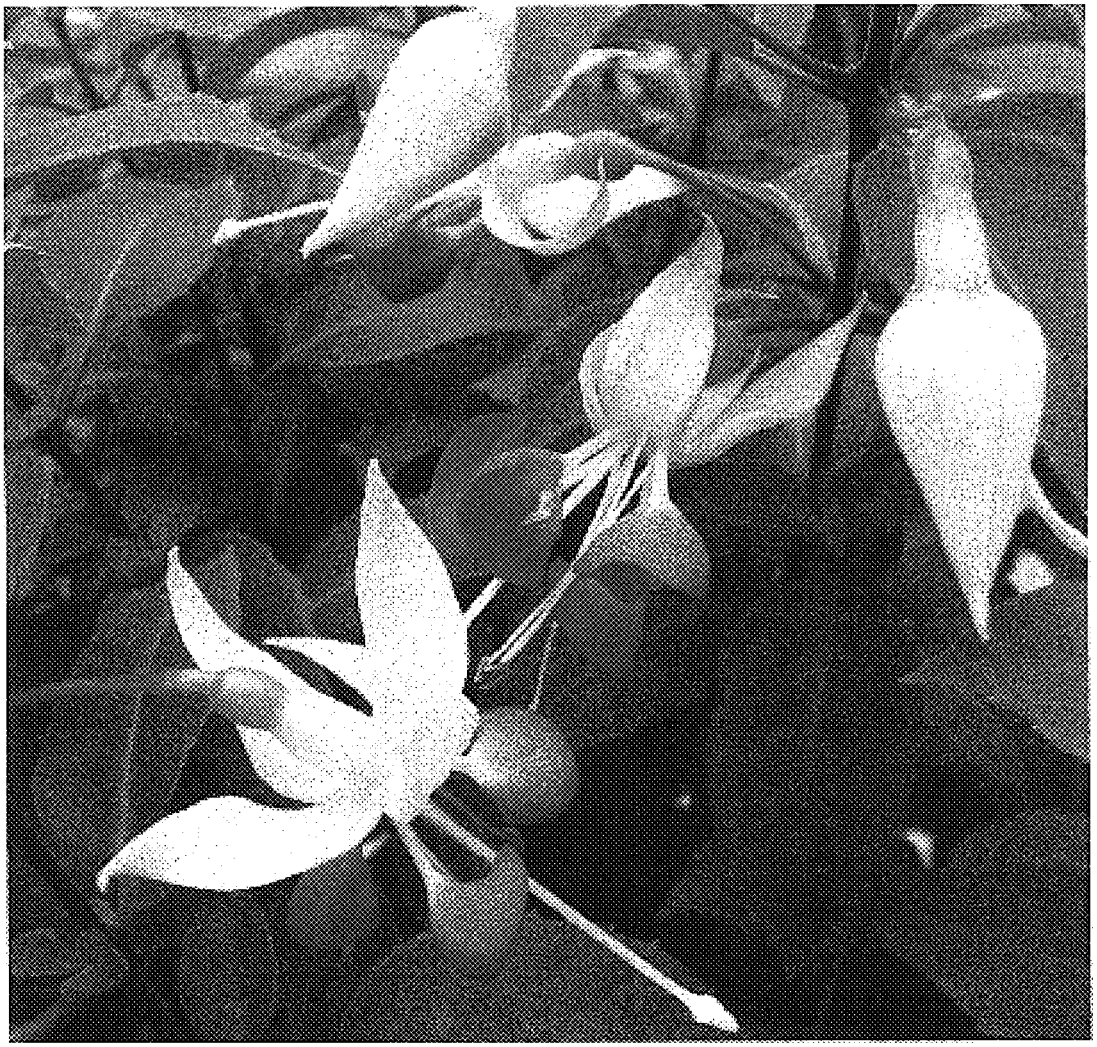
FIG. 2 presents a close-up view of bud and flowers.

Drawings were made using conventional techniques and although colors may appear different from actual colors due to light reflectance they are as accurate as possible by conventional photography.

BOTANICAL DESCRIPTION OF THE PLANT

The following is a detailed description of the new *Fuchsia* plant named 'Rose Quartet'. Data was collected in Arroyo Grande Calif. from 6-week-old plants that were greenhouse grown in 14 cm. containers. The color determinations are in accordance with the 2001 Edition of the Colour Chart of The Royal Horticultural Society, London, England, except where general color terms of ordinary dictionary significance are used. The growing requirements are similar to other *Fuchsia*.

Botanical classification: *Fuchsia×hybrida* 'Rose Quartet'.
Genus: *Fuchsia*.
Species: ×*hybrida*.
Denomination: Rose Quartet.
Common name: *Fuchsia*.
Commercial classification: Ornamental.
Use: Hanging basket, container or landscape plant.
Cultural requirements: Plant in fertile well-draining soil, in full sun, with regular watering.
Root system: Fine and fibrous.
Vigor: Vigorous.
Parentage: *Fuchsia* 'ROSE QUARTET' is a chance individual whole plant hybrid that resulted from the induced open-pollination between individual crops of *Fuchsia×hybrida*. The exact parents are unknown. The following are presumed to be the parent plants:
- *Female parent*.—An individual unnamed *Fuchsia* in an individual crop of *Fuchsia×hybrida*.
- *Male parent*.—An individual unnamed *Fuchsia* in an individual crop of *Fuchsia×hybrida*.

Plant description:
- *Bloom period*.—Late spring to late fall.
- *Light requirements*.—Needs 11–12 hours of natural daylight for blooming to occur.
- *Plant habit*.—Compact and mounding.
- *Height*.—18 cm. in height in a 14 cm. commercial container and 30–45 cm. in height at maturity.
- *Width*.—15 cm. in width in a 14 cm. commercial container and 25–35 cm. in width at maturity.
- *Hardiness*.—USDA Zone 8b.
- *Propagation*.—Propagation is accomplished using softwood cuttings.
- *Time to develop roots*.—14–21 days are needed for initial cuttings to develop roots.
- *Temperature for rooting*.—Recommended air temperature for rooting is 20° Centigrade.
- *Crop time*.—4–6 weeks are needed to produce a finished 14 cm. commercial container plant.
- *Disease susceptibility and resistance*.—There is no specific susceptibility or resistance to disease known to the inventor other than what is typical for the genus *Fuchsia*.

Stem:
- *Trunk dimensions*.—1 cm. in height and 0.75 cm. in diameter.
- *Shape*.—Cylindrical.
- *Stem color*.—182B.
- *Stem dimensions*.—17 cm. in length and 3 mm. in diameter.
- *Stem surface*.—Glabrous.
- *Internode length*.—1.50 cm. between nodes.

Foliage:
- *Shape*.—Broadly elliptic.
- *Division*.—Simple.
- *Apex*.—Acute.
- *Base*.—Rounded.
- *Venation pattern*.—Pinnate.
- *Vein color* (*adaxial surfaces*).—Individual colors 139D and 182D are present on an individual leaf.
- *Vein color* (*abaxial surfaces*).—Individual colors 139D and 182D are present on an individual leaf.
- *Margins*.—Dentate.
- *Attachment*.—Petiolate.
- *Arrangement*.—Opposite.
- *Leaf surface* (*adaxial and abaxial surfaces*).—Slightly puberulent.
- *Leaf width*.—Leaves range from 1.25 to 2.25 cm. in width.
- *Leaf length*.—Leaves range from 1.50 to 4 cm. in length.
- *Leaf attachment*.—Petiolate.
- *Petiole shape*.—Sulcate.
- *Petiole color*.—182B.
- *Petiole dimensions*.—1.25 cm. in length and 2.75 mm. in width.
- *Leaf color* (*adaxial surface*).—139B.
- *Leaf color* (*abaxial surface*).—139C.
- *Fragrance*.—Grass-like.

Flowers:
- *Inflorescence type*.—Solitary.
- *Quantity of buds*.—An average of 10 buds on a 14 cm. commercial container plant.
- *Quantity of flowers*.—An average of 4 open flowers on a 14 cm. commercial container plant.
- *Lastingness of flower*.—Lasts fully opened 3–5 days.
- *Flower shape*.—The calyx is closest to stellular and the corolla is closest to quatrefoil in shape.
- *Persistent or self-cleaning*.—Self-cleaning.
- *Aspect*.—Pendulous.
- *Bud dimensions*.—0.50 cm. in width and 1.75 cm. in length.
- *Bud shape*.—Narrowly bulbous.
- *Bud color*.—Individual colors 145C and 157A are present on an individual bud.
- *Bud surface*.—Slightly puberulent.
- *Bud apex*.—Acute.
- *Bud base*.—Rounded.
- *Calyx color*.—Individual colors 144D and 157A are present on an individual calyx. Tinges of N74D are present on some calyces of an individual plant.
- *Calyx shape*.—Stellular.
- *Sepals*.—Four in number.
- *Sepal color* (*abaxial and adaxial surfaces*).—Individual colors 144D and 157A are present on an individual sepal. Tinges of N74D are present on some sepals of an individual plant.

*Sepal dimensions*.—3 cm. in length and 0.75 cm. in width.
*Sepal apex*.—Acute.
*Sepal base*.—Truncate.
*Sepal shape*.—Reflexed and closest to oblanceolate.
*Sepal margin*.—Entire.
*Sepal surface* (*abaxial surface*).—Glabrous.
*Sepal surface* (*adaxial surface*).—Glabrous.
*Sepal appearance* (*abaxial surface*).—Waxy.
*Sepal appearance* (*adaxial surface*).—Matte.
*Sepals fused or unfused*.—Sepals basally fused.
*Corolla*.—Divided into 4 individual petaloid structures, which consist of a corolla tube and a cup shape petal containing a single stamen.
*Corolla tube dimensions*.—1 cm in length and 0.75 mm in diameter.
*Corolla tube color*.—155B.
*Petals*.—Four in number.
*Petal color* (*adaxial surface*).—N74B.
*Petal color* (*abaxial surface*).—N74C.
*Petal shape*.—Closest to cupule.
*Petal margin*.—Entire.
*Petal apex*.—Closest to truncate.
*Petal base*.—Closest to rounded.
*Petal surface*.—Glabrous.
*Petal dimensions*.—0.75 cm. in width and is 0.75 cm. in length.
*Peduncle dimensions*.—Ranges from 1 to 2 cm. in length and 1.25 mm. in diameter.
*Peduncle shape*.—Cylindrical.
*Peduncle color*.—Colors 144B and 182D are individually present on an individual peduncle.
*Peduncle surface*.—Glabrous.
*Peduncle appearance*.—Waxy.
*Flower fragrance*.—None observed.

Reproductive organs:
*Stamens*.—Eight in number, four of which are petaloid.
*Stamen color*.—155B.
*Regular stamen dimensions*.—3 cm. in length and 0.75 mm. in diameter.
*Petaloid stamen dimensions*.—1 cm. in length and 0.75 mm. in diameter.
*Anther color*.—182D.
*Anther dimensions*.—2.75 mm. in length and 1.25 mm. in width.
*Quantity of pollen*.—Small amount.
*Color of pollen*.—182D.
*Pistil*.—One in number.
*Pistil dimensions*.—3.50 cm. in length and 1.50 mm. in width.
*Pistil color*.—157A.
*Pistil shape*.—Filament.
*Pistil surface*.—Puberulent.
*Stigma shape*.—Cone-shaped.
*Stigma dimensions*.—2.75 mm. in length and 2 mm. in width.
*Stigma color*.—157A.
*Ovary position*.—Inferior.
*Ovary color*.—144A.
*Ovary shape*.—Cupulate.
*Ovary dimensions*.—5 mm. in length and 4 mm. in diameter.

Seed production: No seed production has been observed to date.

It is claimed:

1. A new and distinct cultivar of *Fuchsia* plant named 'Rose Quartet' as described and illustrated.

* * * * *